US009241726B2

(12) United States Patent  
Larson

(10) Patent No.: US 9,241,726 B2  
(45) Date of Patent: *Jan. 26, 2016

(54) METHODS OF USING A SEPTAL STAPLER

(71) Applicant: ENTRIGUE SURGICAL, INC., San Antonio, TX (US)

(72) Inventor: Michael C. Larson, New Orleans, LA (US)

(73) Assignee: ARTHROCARE CORPORATION, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/059,882

(22) Filed: Oct. 22, 2013

(65) Prior Publication Data

US 2014/0046365 A1    Feb. 13, 2014

Related U.S. Application Data

(63) Continuation of application No. 12/252,174, filed on Oct. 15, 2008, now Pat. No. 8,579,179, which is a continuation of application No. 11/338,131, filed on Jan. 23, 2006, now Pat. No. 7,438,208.

(60) Provisional application No. 60/646,734, filed on Jan. 25, 2005, provisional application No. 60/733,714, filed on Nov. 4, 2005.

(51) Int. Cl.  
*A61B 17/04* (2006.01)  
*A61B 17/10* (2006.01)  
(Continued)

(52) U.S. Cl.  
CPC .............. *A61B 17/24* (2013.01); *A61B 17/064* (2013.01); *A61B 17/068* (2013.01); *A61B 17/0057* (2013.01); *A61B 17/10* (2013.01);

(Continued)

(58) Field of Classification Search  
CPC .................. A61B 17/068; A61B 2017/00314; A61B 17/00234; A61B 17/24; A61B 2017/320072  
USPC .............. 227/175.1–182.1, 19; 606/219, 185, 606/151  
See application file for complete search history.

(56) References Cited

U.S. PATENT DOCUMENTS

| 2,432,853 A | 12/1947 | Barclay | 227/133 |
| 3,575,038 A | 4/1971 | Mallett | 227/19 |

(Continued)

FOREIGN PATENT DOCUMENTS

| WO | WO 03/057274 | 7/2003 |
| WO | WO 03/094745 | 11/2003 |

OTHER PUBLICATIONS

Office Communication issued in Australian Patent Application No. 2006208189, dated Sep. 2, 2011.  
Supplementary European Search Report, issued in European Application No. 06719360.7, dated Nov. 20, 2009.  
"Novel Device for Simplifying Septoplasty Procedures," University of Florida Office of Technology Licensing, www.otl.ufl.edu.

(Continued)

*Primary Examiner* — Robert Long

(57) ABSTRACT

Methods of stapling a nasal septum using a nasal septal stapling apparatus comprising obtaining a nasal septal stapling apparatus comprising a body, at least one arm extending from the body and comprising an end distal from the body, a staple bank comprising a plurality of staples proximal to the end of the at least one arm, and a staple moving member configured to discharge a staple from the staple bank, and a trigger. The methods comprise placing the at least one arm against a nasal septum of a patient and moving the trigger, wherein moving the trigger causes the staple moving member to discharge a staple from the staple bank and through the nasal septum of the patient.

19 Claims, 7 Drawing Sheets

(51) Int. Cl.
*A61B 17/24* (2006.01)
*A61B 17/064* (2006.01)
*A61B 17/068* (2006.01)
*A61B 17/00* (2006.01)

(52) U.S. Cl.
CPC ............... *A61B2017/00243* (2013.01); *A61B 2017/00535* (2013.01); *A61B 2017/00575* (2013.01); *A61B 2017/00588* (2013.01); *A61B 2017/00606* (2013.01); *A61B 2017/0647* (2013.01)

(56) References Cited

U.S. PATENT DOCUMENTS

| | | | |
|---|---|---|---|
| 3,598,299 A | 8/1971 | Johnson | 227/144 |
| 3,744,495 A | 7/1973 | Johnson | 606/142 |
| 4,241,861 A | 12/1980 | Fleischer | 227/135 |
| 4,749,114 A | 6/1988 | Green | 227/19 |
| 4,773,420 A | 9/1988 | Green | 227/178.1 |
| 4,873,976 A | 10/1989 | Schreiber | 606/213 |
| 4,884,572 A | 12/1989 | Bays et al. | 606/139 |
| 4,895,148 A | 1/1990 | Bays et al. | 606/213 |
| 4,917,114 A | 4/1990 | Green et al. | 227/179.1 |
| 4,924,865 A | 5/1990 | Bays et al. | 606/77 |
| 4,930,674 A | 6/1990 | Barak | 227/179.1 |
| 4,932,960 A | 6/1990 | Green et al. | 606/220 |
| 4,976,715 A | 12/1990 | Bays et al. | 606/77 |
| 4,991,764 A | 2/1991 | Mericle | 227/178.1 |
| 4,994,073 A | 2/1991 | Green | 606/220 |
| 5,040,715 A | 8/1991 | Green et al. | 227/176.1 |
| 5,059,206 A | 10/1991 | Winters | 606/213 |
| 5,089,009 A | 2/1992 | Green | 606/219 |
| 5,094,233 A | 3/1992 | Brennan | 602/6 |
| 5,108,422 A | 4/1992 | Green et al. | 606/219 |
| 5,116,349 A | 5/1992 | Aranyi | 227/181.1 |
| 5,125,553 A | 6/1992 | Oddsen et al. | 227/175.1 |
| 5,129,906 A | 7/1992 | Ross et al. | 606/77 |
| 5,203,784 A | 4/1993 | Ross et al. | 606/140 |
| 5,246,441 A | 9/1993 | Ross et al. | 606/53 |
| 5,246,455 A | 9/1993 | Shikani | 623/10 |
| 5,269,783 A | 12/1993 | Sander | 606/148 |
| 5,293,881 A | 3/1994 | Green et al. | 128/898 |
| 5,330,486 A | 7/1994 | Wilk | 606/139 |
| 5,336,163 A | 8/1994 | DeMane et al. | 602/46 |
| 5,342,376 A | 8/1994 | Ruff | 606/151 |
| 5,344,060 A | 9/1994 | Gravener et al. | 227/180.1 |
| 5,350,396 A | 9/1994 | Eliachar | 606/199 |
| 5,351,871 A | 10/1994 | Bauer | 227/177.1 |
| 5,361,782 A | 11/1994 | Bauer | 128/898 |
| 5,366,134 A | 11/1994 | Green et al. | 227/176.1 |
| 5,366,459 A | 11/1994 | Yoon | 606/151 |
| 5,370,294 A | 12/1994 | Bauer | 227/177.1 |
| 5,374,268 A | 12/1994 | Sander | 606/148 |
| 5,376,095 A | 12/1994 | Ortiz | 606/143 |
| 5,423,858 A | 6/1995 | Bolanos et al. | 606/220 |
| 5,425,747 A | 6/1995 | Brotz | 606/228 |
| 5,478,354 A | 12/1995 | Tovey et al. | 606/219 |
| 5,527,318 A | 6/1996 | McGarry | 606/139 |
| 5,535,935 A | 7/1996 | Vidal et al. | 227/175.2 |
| 5,540,240 A * | 7/1996 | Bauer | 128/898 |
| 5,551,622 A | 9/1996 | Yoon | 227/178.1 |
| 5,584,859 A | 12/1996 | Brotz | 606/228 |
| 5,586,711 A | 12/1996 | Plyley et al. | 227/176.1 |
| 5,593,423 A | 1/1997 | Person et al. | 606/219 |
| 5,599,284 A | 2/1997 | Shea | 602/17 |
| 5,601,556 A | 2/1997 | Torrie et al. | 606/326 |
| 5,628,751 A | 5/1997 | Sander et al. | 606/104 |
| 5,643,319 A | 7/1997 | Green et al. | 606/218 |
| 5,653,373 A | 8/1997 | Green et al. | 227/175.1 |
| 5,655,698 A | 8/1997 | Yoon | 227/176.1 |
| 5,658,312 A | 8/1997 | Green et al. | 606/219 |
| 5,702,048 A | 12/1997 | Eberlin | 227/177.1 |
| 5,713,839 A | 2/1998 | Shea | 602/217 |
| 5,720,753 A | 2/1998 | Sander et al. | 606/104 |
| 5,782,396 A | 7/1998 | Mastri et al. | 227/175.3 |
| 5,807,302 A | 9/1998 | Wandel | 604/8 |
| 5,810,240 A | 9/1998 | Robertson | 227/175.2 |
| 5,817,109 A | 10/1998 | McGarry et al. | 606/143 |
| 5,827,298 A | 10/1998 | Hart et al. | 606/139 |
| 5,843,084 A | 12/1998 | Hart et al. | 606/77 |
| 5,915,615 A | 6/1999 | Bauer | 227/177.1 |
| 5,938,101 A * | 8/1999 | Izuchukwu et al. | 227/176.1 |
| 5,964,394 A | 10/1999 | Robertson | 227/176.1 |
| 5,976,127 A | 11/1999 | Lax | 606/32 |
| 5,980,524 A | 11/1999 | Justin et al. | 606/75 |
| 5,984,927 A | 11/1999 | Wenstrom, Jr. et al. | 606/329 |
| 6,017,346 A | 1/2000 | Grotz | 606/323 |
| 6,131,790 A | 10/2000 | Piraka | 227/176.1 |
| 6,187,009 B1 | 2/2001 | Herzog et al. | 606/75 |
| 6,190,401 B1 | 2/2001 | Green et al. | 606/224 |
| 6,241,747 B1 | 6/2001 | Ruff | 606/216 |
| 6,264,086 B1 | 7/2001 | McGuckin, Jr. | 227/180.1 |
| 6,270,517 B1 | 8/2001 | Brotz | 606/228 |
| 6,283,121 B1 | 9/2001 | Fukutomi | 128/205.13 |
| 6,322,563 B1 | 11/2001 | Cummings et al. | 606/916 |
| 6,406,479 B1 | 6/2002 | Justin et al. | 606/104 |
| 6,446,854 B1 | 9/2002 | Remiszewski et al. | 227/175.1 |
| 6,517,564 B1 | 2/2003 | Gafton et al. | 606/213 |
| 6,551,343 B1 | 4/2003 | Tormala et al. | 606/213 |
| 6,554,852 B1 | 4/2003 | Oberlander | 606/232 |
| 6,565,581 B1 | 5/2003 | Spence et al. | 606/153 |
| 6,629,988 B2 | 10/2003 | Weadock | 606/219 |
| 6,645,226 B1 | 11/2003 | Jacobs et al. | 606/215 |
| 6,666,872 B2 | 12/2003 | Barreiro et al. | 606/142 |
| 6,692,499 B2 | 2/2004 | Tormala et al. | 606/213 |
| 6,726,705 B2 | 4/2004 | Peterson et al. | 606/216 |
| 6,773,440 B2 | 8/2004 | Gannoe et al. | 606/142 |
| 6,893,452 B2 | 5/2005 | Jacobs | 606/215 |
| 6,921,408 B2 | 7/2005 | Sauer | 606/144 |
| 6,966,919 B2 | 11/2005 | Sixto, Jr. et al. | 606/153 |
| 6,981,983 B1 | 1/2006 | Rosenblatt et al. | 606/216 |
| 7,014,638 B2 | 3/2006 | Michelson | 606/1 |
| 7,028,878 B2 | 4/2006 | Bauer | 227/175.1 |
| 7,033,378 B2 | 4/2006 | Smith et al. | 606/220 |
| 7,105,010 B2 | 9/2006 | Hart et al. | 606/213 |
| 7,156,862 B2 | 1/2007 | Jacobs et al. | 606/215 |
| 7,172,615 B2 | 2/2007 | Morriss et al. | 606/215 |
| 7,211,088 B2 | 5/2007 | Grafton et al. | 606/77 |
| 7,220,272 B2 | 5/2007 | Weadock | 606/219 |
| 7,226,468 B2 | 6/2007 | Ruff | 606/216 |
| 7,226,469 B2 | 6/2007 | Benavitz et al. | 606/232 |
| 7,431,730 B2 | 10/2008 | Viola | 606/219 |
| 7,438,208 B2 | 10/2008 | Larson | 227/175.1 |
| 7,954,686 B2 | 6/2011 | Baxter et al. | 227/176.1 |
| 8,714,429 B2 * | 5/2014 | Demmy | 227/176.1 |
| 2003/0187381 A1 | 10/2003 | Greenawalt et al. | 604/11 |
| 2005/0113850 A1 | 5/2005 | Tagge | 606/151 |
| 2005/0192628 A1 | 9/2005 | Viola | 606/219 |
| 2005/0222610 A1 | 10/2005 | Melker | 606/205 |
| 2005/0273138 A1 | 12/2005 | To et al. | 606/21 |
| 2006/0276817 A1 | 12/2006 | Vassallo et al. | 606/185 |
| 2007/0021777 A1 | 1/2007 | Fowler et al. | 606/205 |
| 2007/0073336 A1 | 3/2007 | Hart et al. | 606/213 |
| 2007/0162056 A1 | 7/2007 | Gerbi et al. | 606/153 |
| 2009/0099577 A1* | 4/2009 | Gonzales et al. | 606/143 |

OTHER PUBLICATIONS

Heublein et al., "Biocorrosion of magnesium alloys: a new principle in cardiovascular implant technology?" *Heart*, 89:651-656, 2003.

Melker, "Method and Apparatus for Performing Septal Surgeries," U.S. Appl. No. 60/553,501, filed Mar. 16, 2004.

Office Communication, issued in U.S. Appl. No. 11/338,131, dated Jan. 10, 2008.

Office Communication, issued in U.S. Appl. No. 11/338,131, dated Jan. 7, 2007.

Office Communication, issued in U.S. Appl. No. 11/338,131, dated Feb. 2, 2007.

Office Communication issued in Canadian Patent Application No. 2,595,838, dated Sep. 25, 2012.

* cited by examiner

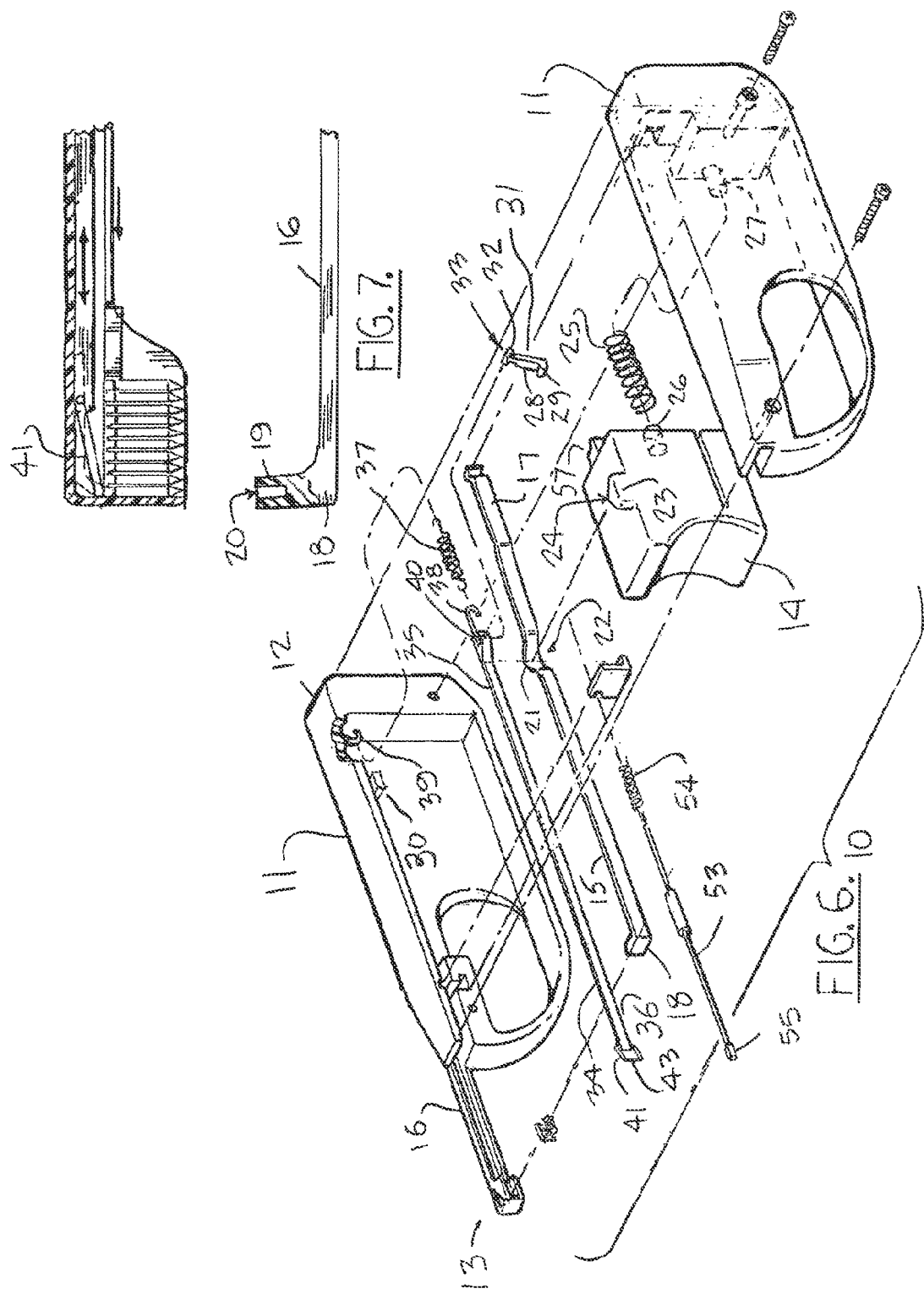

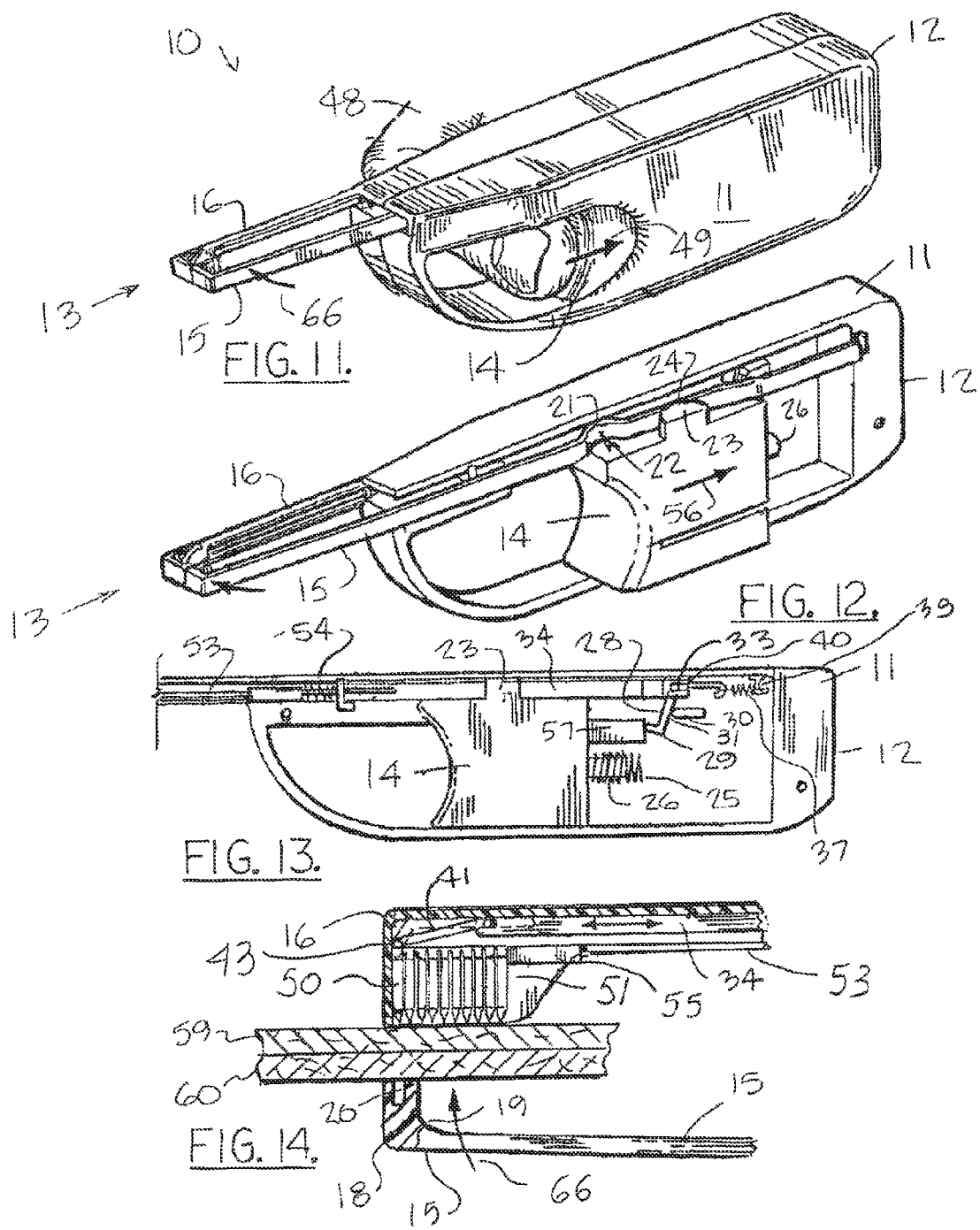

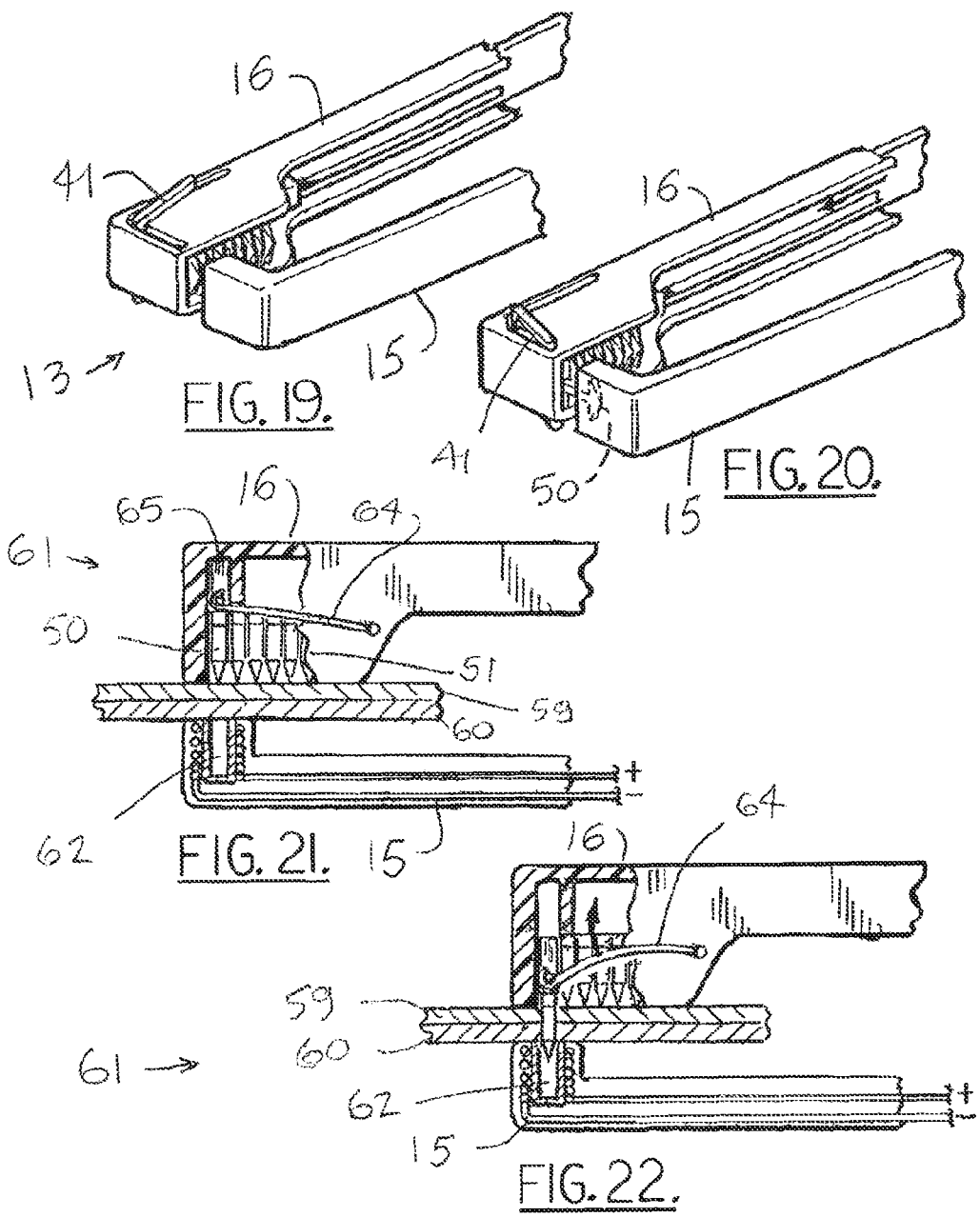

METHODS OF USING A SEPTAL STAPLER

CROSS-REFERENCE TO RELATED APPLICATIONS

This application is a continuation of co-pending U.S. patent application Ser. No. 12/252,174 filed Oct. 15, 2008, which is a continuation of U.S. patent application Ser. No. 11/338,131, filed Jan. 23, 2006, now U.S. Pat. No. 7,438,208, which claims the benefit of U.S. Provisional Patent Application No. 60/646,734, filed Jan. 25, 2005, and U.S. Provisional Patent Application No. 60/733,714, filed Nov. 4, 2005. The entire contents of each of the above-referenced disclosures is specifically incorporated by reference herein without disclaimer.

BACKGROUND OF THE INVENTION

1. Field of the Invention

The present invention relates to septal surgery. More particularly, the present invention relates to an improved septal stapler apparatus that places surgical staples in a patient's septal tissue responsive to a trigger pull that moves two elongated spaced apart appendages together, one pushing a staple toward the other and through the selected tissue.

2. Background of the Invention

The following US patents, which contain background information, are incorporated herein by reference:

TABLE I

| PAT. NO. | TITLE | ISSUE DATE |
| --- | --- | --- |
| 5,540,240 | Intranasal Septal Fastener Driving Method | 30 Jul. 1996 |
| 5,361,782 | Intranasal Septal Stapling Method | 8 Nov. 1994 |
| 5,370,294 | Intranasal Septal Stapling Device and Method | 6 Dec. 1994 |
| 6,283,121 | Manual Pump and Ambu Bag | 4 Sep. 2001 |
| 6,131,790 | Surgical Stapler and Cartridge | 17 Oct. 2000 |
| 5,351,871 | Intranasal Septal Stapling Device | 4 Oct. 1994 |
| 5,915,615 | Tissue Fastening Device | 29 Jun. 1999 |

SUMMARY OF THE INVENTION

The present invention provides an improved septal stapling apparatus that provides an instrument body having proximal and distal end portions. A handle at the proximal end portion enables a user to hold and manipulate the instrument body. A pair of spaced apart arms extend distally from the handle. The arms include a staple arm and a tensioning arm. There is a gap between the arms that enables placement of the arms on opposing sides of the tissue to be stapled.

The body provides a trigger that moves between resting and firing positions. The trigger moves an actuator link between first and second positions. The actuator link includes a staple moving member that is attached to the staple arm.

The staple arm has a staple bank that includes multiple staples. The trigger, actuator link, staple bank, and staple moving member are configured to move a staple to a stapling position when the trigger is pulled. The staple arm and tensioning arm move together when the trigger is pulled in order to place the staple in the selected tissue.

The present invention includes a septal stapling apparatus, having an instrument body with proximal and distal end portions. A handle at the distal end portion enables a user to hold and manipulate the instrument body.

A pair of spaced apart arms extends from the handle. The arms include a staple arm and a tensioning arm. The body has a trigger that moves between resting and firing positions. An actuator link moves between first and second positions, the actuator link being moved by the trigger. The actuator link includes a staple moving member that is attached to the staple arm.

The staple arm carries a staple bank that includes multiple staples. The trigger, actuator link, staple bank and staple moving member are configured to move a staple to stapling position when the trigger is pulled. The staple arm and tensioning arm move together when the trigger is pulled. Preferably, the tensioning arm has a receptacle that receives at least a part of a staple during stapling. Preferably, the tensioning arm pivots relative to the body during stapling.

The staple arm is preferably fixed relative to the body. The actuator preferably slides relative to the body. The actuator and staple moving member can be pivotally attached. The staple arm can house the staple magazine with a bank of staples therein. The actuator slides relative to the body and simultaneously causes the staple moving member to pivot, engaging and dispensing a staple from the staple magazine. Preferably, the staple arm and tensioning arm each have head portions that come together to dispense a staple when the trigger is pulled.

The handle fits comfortably in an operator's palm, and can permit equal access to the trigger from either side, i.e. either right hand or left hand operation. Emanating from the handle are the staple arm and the tensioning arm. These are of suitable dimensions to be inserted into a typical patient's nose, one arm into each nostril. At the end of the staple arm is the staple head which houses a bank of staples which are dispensed one-at-a-time.

The end of the tensioning arm can provide a recess for accommodating the heads of the staples as they are pushed from the staple head.

The tensioning arm moves so that the device can pass the relatively wide columella at the base of the nose between the nostrils but still gently come together on opposite sides of the relatively thin mucosal layers inside the nose which are to be stapled.

A handle cover and handle base can be fastened together (as with recessed Philips-head screws) to form the handle. The trigger slides within the handle, against the force of a trigger spring. The motion of the trigger causes the movement of the tensioning arm which pivots at the back of the handle cover.

Movement of the trigger also causes the translation of the actuator link by pivoting the trigger link about a fulcrum which protrudes from the inner surface of the handle base. The motion of the actuator link is transferred to the head link, causing one of the staples in the bank of staples to be dispensed from the staple head. The bank of staples are positioned by the staple advance rod which is moved by the advance rod spring being compressed between the body of the staple advance rod and the advance rod base.

The contoured shape of the tensioning arm mates with a projection or peg of the trigger. During the first part of the trigger's travel, the projection or peg pushes against the force of the tensioning arm spring to bring the tensioning arm into the proper position for stapling. The final portion of the trigger's travel acts to maintain the same position of the tensioning arm.

The trigger link moves and pivots, e.g. on a fulcrum on the inner wall of the handle base. When the bottom of the link is pressed by the trigger, the top moves the actuator link. The actuator link is retracted by the actuator spring.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein:

FIG. 6 is an exploded perspective view of the preferred embodiment of the apparatus of the present invention;

FIG. 7 is a sectional view taken along lines 7-7 of FIG. 1;

FIG. 11 is a perspective view of the preferred embodiment of the apparatus of the present invention;

FIG. 12 is a partial, perspective cut-away view of the preferred embodiment of the apparatus of the present invention;

FIG. 13 is a partial, sectional, elevation view of the preferred embodiment of the apparatus of the present invention;

FIG. 14 is a partial, sectional, elevation view of the preferred embodiment of the apparatus of the present invention;

FIG. 19 is a fragmentary perspective view of the preferred embodiment of the apparatus of the present invention;

FIG. 20 is a partial perspective view of the preferred embodiment of the apparatus of the present invention;

FIG. 21 is a sectional, elevation view of an alternate embodiment of the apparatus of the present invention;

FIG. 22 is a sectional, elevation view of an alternate embodiment of the apparatus of the present invention;

DETAILED DESCRIPTION OF THE INVENTION

Figure 1:
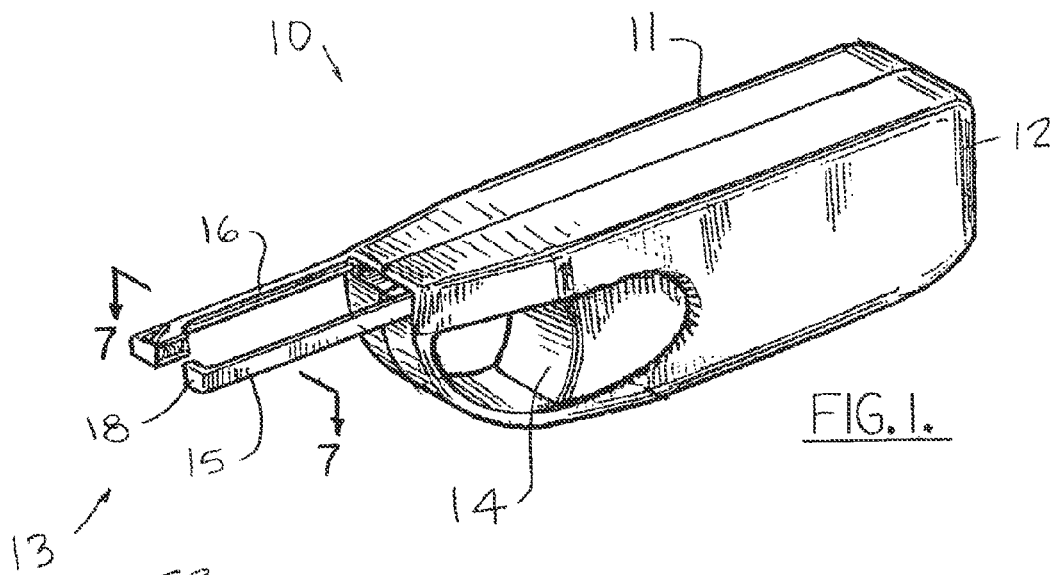
FIG. 1 is a perspective view of the preferred embodiment of the apparatus of the present invention in an open position.
Figure 2:
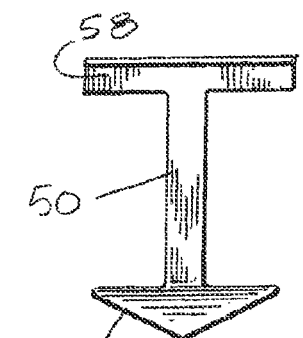
FIG. 2 is a front, fragmentary view of the preferred embodiment of the apparatus of the present invention showing a staple.
Figure 3:
FIG. 3 is a side, fragmentary view of the preferred embodiment of the apparatus of the present invention showing a staple.
Figure 4:
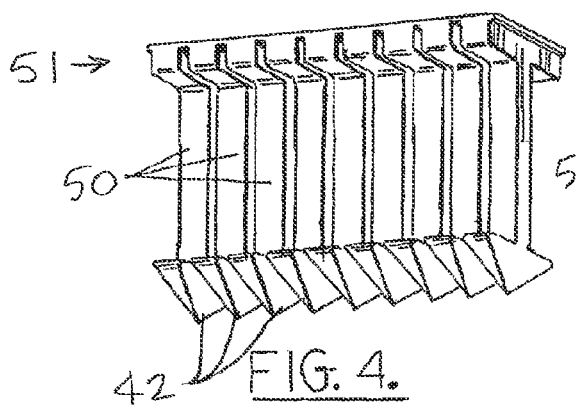
FIG. 4 is a partial perspective view of the preferred embodiment of the apparatus of the present invention showing a staple bank.
Figure 5:
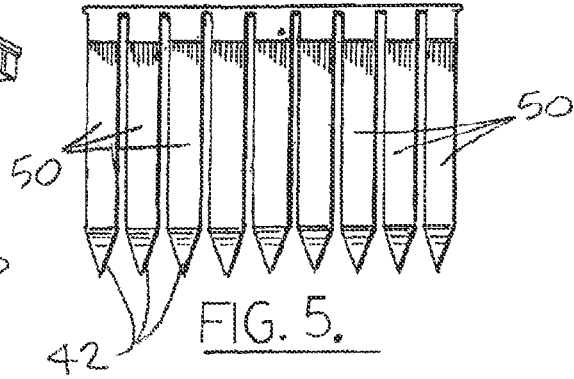
FIG. 5 is a partial side view of the preferred embodiment of the apparatus of the present invention in an open position showing a staple bank.
Figure 8:
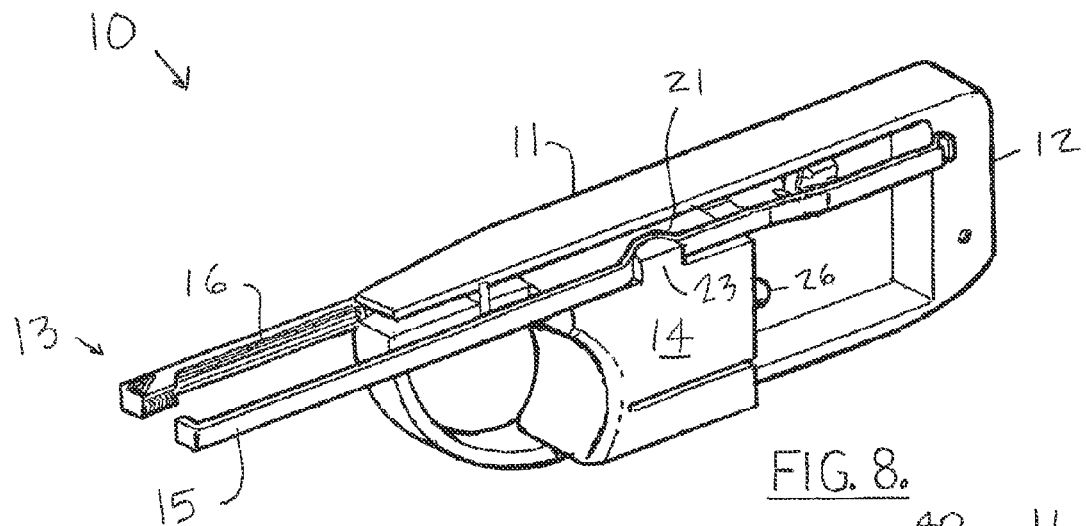
FIG. 8 is a partial perspective view of the preferred embodiment of the apparatus of the present invention.

FIGS. 1 and 6-20 show the preferred embodiment of the apparatus of the present invention designated generally by the numeral 10. Septal stapler apparatus 10 provides a tool body 11 having a proximal end portion 12 and a distal end portion 13. A trigger 14 is movably mounted to the tool body 11. The trigger 14 is used to activate the device when it is held by a user 48. A user 48 grips the tool body 11, depresses the trigger 14 in the direction of arrow 49 in FIG. 11, which then dispenses a staple 50 from staple bank 51 to the selected septal tissue layers 59, 60. FIGS. 2 and 3 show one embodiment of a single shaft staple 50 with one end pointed to facilitate membrane penetration. FIGS. 4 and 5 show a bank of staples 8 which is housed in the staple head 4. The bank of staples can be formed of any material. Polymeric staples, even absorbable ones, may be molded as a bank of staples by any number of processes, including injection molding, fused deposition, etc. Metal, ceramic or polymeric staples may be formed, cast, molded or machined individually and then adhesively attached together to form a bank of staples or loaded into the stapler body individually and held in a bank by friction at the surfaces.

A pair of arms are attached to the tool body 11. These include a moving arm 15 and a fixed arm 16. The moving arm 15 has a proximal end portion 17 and a distal end portion 18. The distal end portion 18 provides a receptacle 19 having a socket 20 that is receptive of an end portion (pointed section 42) of a staple 50 when the trigger 14 is depressed in the direction of arrow 49 in FIG. 11 and the moving arm 15 pivots in the direction of arrow 66 in FIG. 11 to meet the fixed arm 16 (see FIG. 14).

The moving arm 15 provides a contoured section 21 having a concavity 22 (see FIG. 12). This concavity 22 engages a camming surface 24 on projection or peg 23 of trigger 14 in the open position before the trigger 14 is depressed. When a user 48 depresses the trigger 14, the camming surface 24 of the projection 23 moves proximally (see arrow 56, FIG. 12), disengaging from the concavity 22 and thus rotating the moving arm 15 toward the fixed arm 16.

The trigger 14 is biased to return to a relaxed beginning position by compressive trigger spring 25. This trigger spring 25 can be mounted at its end portions on respective cylinders 26, 27. One of the cylinders 26 is mounted on the trigger 14. The other cylinder 27 is mounted on the tool body 11 (see FIGS. 6, 8, 9, and 13).

When the trigger 14 is depressed, lever 28 (FIGS. 6, 13) is rotated to push staple actuator link 34 in a distal direction. The lever 28 has a lower end portion 29 that is engaged by rod 57 on the rear surface of the trigger 14 when the trigger is depressed. The lever 28 rotates about fulcrum 30 so that its upper end portion 33 pushes the staple actuator link 34 distally. The central portion 31 of the link 28 engages the fulcrum 30. Upper end portion 33 of the lever 28 provides a transverse pin 32 that is mounted in slotted portion 40 provided at the proximal end 35 of staple actuator link 34.

Spring 37 connects at its end portions to hooks 38, 39. The hook 38 is attached to and travels with staple actuator link 34. The hook 39 is attached to the tool body 11. When the trigger 14 is depressed, lever 28 rotates so that the transverse pin 32 pushes the staple actuator link 34 in a distal direction.

Distal end portion 36 (FIG. 6) of actuator link 34 has a rectangularly shaped head 41 that engages a staple 50 to be placed in the selected tissue. The staple 50 is one of a plurality of staples that form a staple bank 51 (see FIGS. 2-5). The rectangularly shaped head 41 can be pivotally attached to the distal end 36 of the staple actuator link 34. The head 41 provides a transverse bar 43 (FIG. 6) that contacts the transverse beam 58 (FIG. 2) of staple 50 when the trigger 14 is depressed. The bar 43 of rectangular head 41 initially travels in a longitudinal slot 44 (FIG. 10), then curved slot 47, then in transverse slot 46. The longitudinal slot 44 and transverse slot 46 are connected with the curved transition slot section 47.

Figure 17:
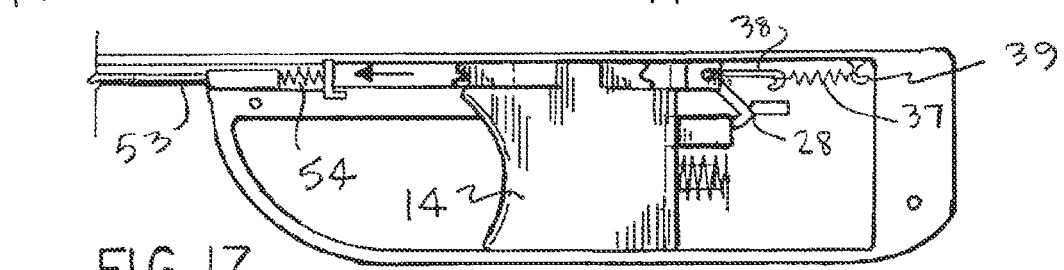
FIG. 17 is a partial sectional view of the preferred embodiment of the apparatus of the present invention shown in stapling position.
Figure 18:
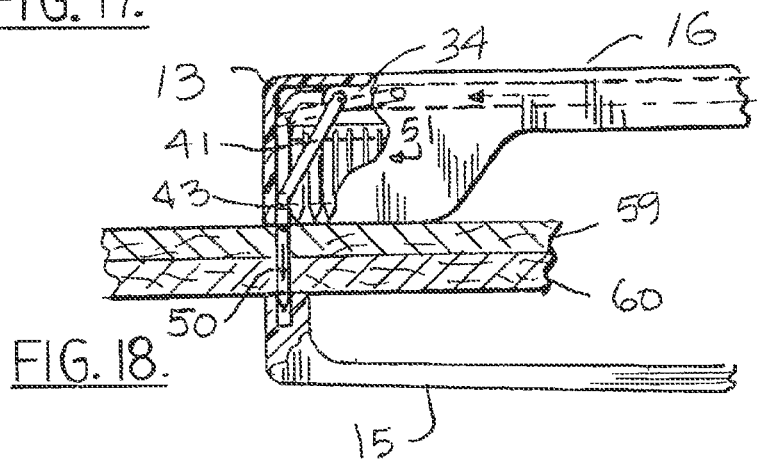
FIG. 18 is a partial sectional view of the preferred embodiment of the apparatus of the present invention shown in stapling position.

When the trigger 14 is depressed, the staple actuator link 34 (FIG. 14) moves distally, forcing the transverse bar 43 of rectangular head 41 to engage a staple 50 of staple bank 51. The transverse bar 43 engages the nearest staple 50 and pushes its pointed section 42 into the selected tissue 59, 60 (FIG. 18). The staple bank 51 is advanced using a staple advance rod 53 (FIGS. 6, 17). Rod 53 is urged in a distal direction with rod-advance spring 54. The advance rod 53 can provide an enlarged head 55 (FIGS. 6, 14) that is sized and shaped to contact and push staple bank 51.

Figure 9:
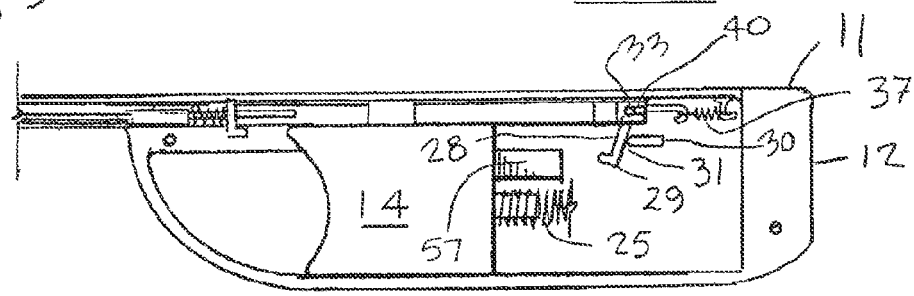
FIG. 9 is a partial, cut-away view of the preferred embodiment of the apparatus of the present invention.

FIGS. 8-18 show the interplay of the trigger 14 and the trigger link 28. FIG. 9 corresponds to the first part of the motion of trigger 14 (which moves the moving or tensioning arm 15, as in FIG. 6). FIGS. 9 and 13 show the point in the travel when the trigger 14 first contacts the trigger link 28. FIGS. 11, 17 and 18 show the full extent of the travel of the trigger 14, having pushed the bottom of the link 28 back, causing its upper end 33 to move forward, thus pushing the actuator link 34 forward.

FIG. 18 depicts the staple head at the distal end 13 portion of the arm 16 and partially broken away to show the locations of the bank 51 of staples 50, the head 41 and the actuator link 34.

Figure 10:
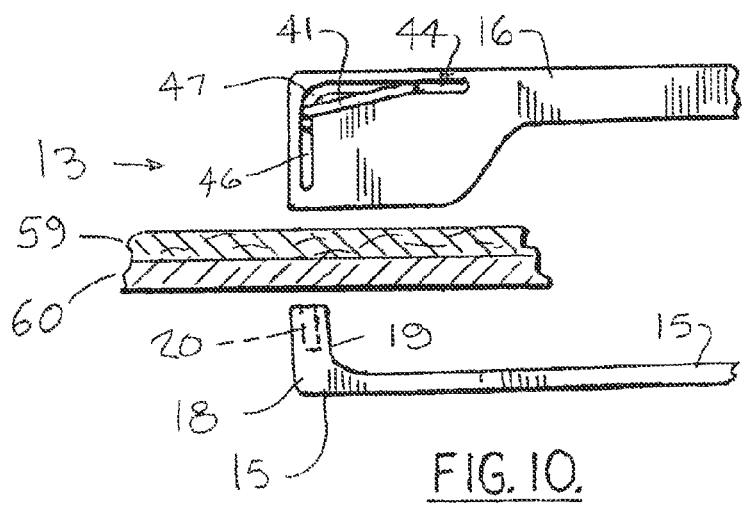
FIG. 10 is a partial sectional, side view of the preferred embodiment of the apparatus of the present invention.
Figure 15:
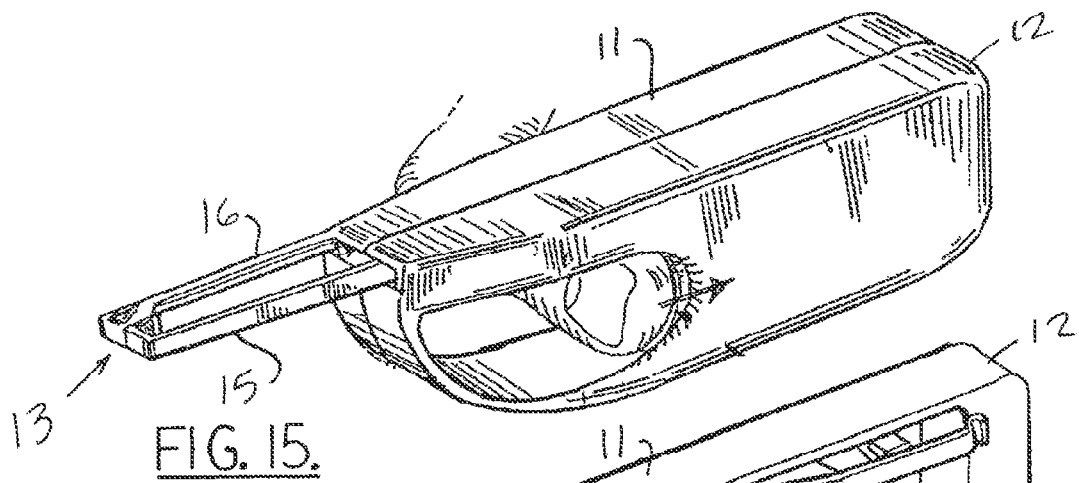
FIG. 15 is a perspective view of the preferred embodiment of the apparatus of the present invention shown in stapling position.
Figure 16:
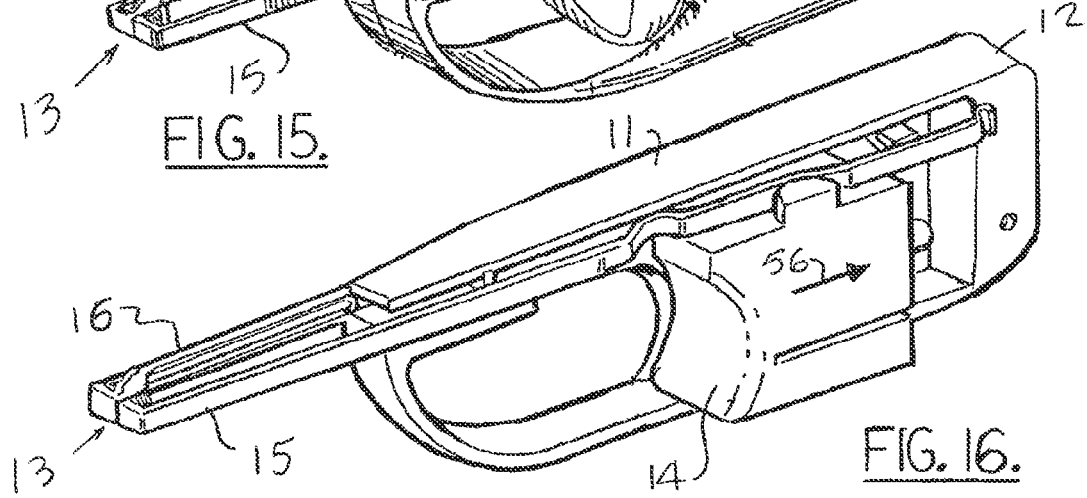
FIG. 16 is a partial perspective view of the preferred embodiment of the apparatus of the present invention shown in stapling position.

FIGS. 10, 14, and 18 show views of the ends of the staple arm 16 and moving arm 15 during the process of dispensing a staple 50 from the bank 51 of staples and when joining two mucosal membrane layers 59, 60 or tissue flaps together with a staple 50. FIGS. 10 and 14 represent the pre-stapled state, after the cartilage and bone are removed during the septoplasty operation. FIG. 14 represents the state after the first stage of trigger 14 actuation when the arm 15 moves to bring the two membranes 59, 60 into contact. FIG. 18 represents the state after complete trigger 14 actuation when the lead staple 50 penetrates the two membranes 59, 60. After the trigger 14 is released, leaving the staple 50 holding the two membranes 59, 60 together, the arms 15, 16 return to the starting position of FIGS. 7-10.

The present invention encompasses other mechanisms for imparting the necessary driving force to a staple within the geometrical constraints of a typical nasal passageway, in addition to a compression linkage. A description of three of these alternate embodiments or mechanisms follows with reference to FIGS. 21-26. Each may be housed within a chassis similar to that envisioned for the compression linkage, namely an arm carrying a bank of staples opposite an arm with a staple receptacle.

The first embodiment variant 61 (FIG. 21) is based on magnetic or electro-magnetic principles, whereby the force to move staples 50 is provided by a magnetic field at magnet 62. The magnet 62 can be either permanent, e.g., a rare earth magnet, or induced by an electric current, e.g., a solenoid. FIGS. 21 and 22 show staples 50 being sequentially acted upon by an actuating member, such as plunger 65, or a bar, link, or the like, which moves in relation to arm 16 which holds the staples 50 in the ready position as with the preferred embodiment. A moving arm 15 moves into proximity of the staple 50 and carries a magnetic field e.g. magnet 62. Arm 15 can be made either completely or partially from magnetic material and/or contain an electromagnet coil. The magnetic attraction pulls the actuating arm member 15 to arm 16, causing the staple 50 to fire into the membranes 59, 60 to be stapled. After firing, the magnetic force on the actuating member is diminished through moving the arm 15 away from arm 16 and/or turning off the electromagnet 62. FIGS. 21 and 22 show external representations of the arms 15, 16 and how the actuating member (e.g. plunger 65) may be held in, and returned to, the ready position by an actuator return spring 64 (leaf, tension, or compression). FIG. 21 shows a leaf spring 64 supporting the actuating member 65 in the ready position. FIG. 22 shows the actuating member 65 in the actuated position, i.e., at the end of a staple stroke, wherein the magnetic force of the swing arm overcomes the lesser restraining force of the leaf spring 64 to pull the plunger 65 and dispense staple 50. Once the magnetic force is diminished, the actuating member or plunger 65 returns to the position shown in FIG. 21 under the action of the leaf spring 64.

Figure 23:
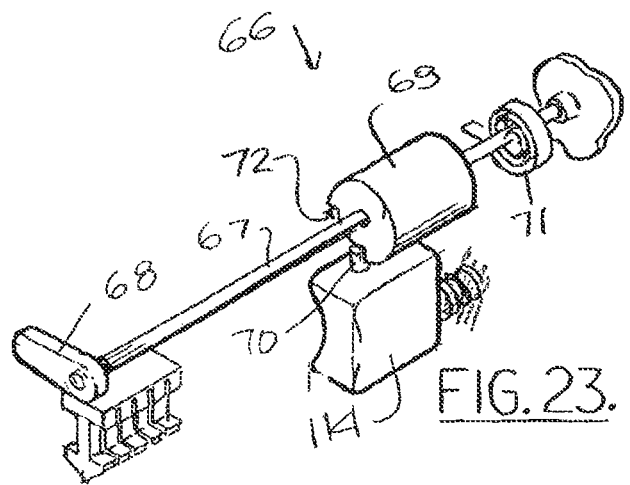
FIG. 23 is a perspective view of a third embodiment of the apparatus of the present invention.
Figure 24:
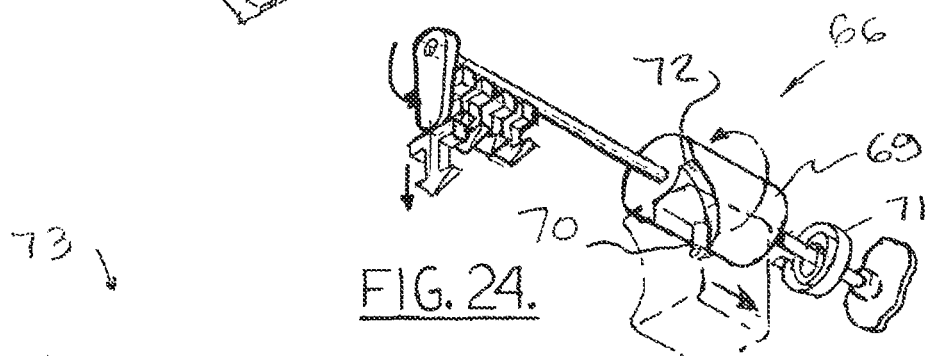
FIG. 24 is another perspective view of the third embodiment of the apparatus of the present invention.

An additional variant, depicted in FIGS. 23 and 24, is based on the rotation of shaft 67 and cam 68 which presses on the head of the staple 50 to be fired. The rotation of the cam 68 can be caused by the torsional twist of attached shaft 67. FIG. 23 shows the cam 68 in the un-actuated position in contact with the staple 50 to be fired from the bank 51 of staples. FIG. 24 shows the same staple 50 being displaced by the movement of the cam 68 due to the twist of the torsion shaft 67. The twist of the shaft 67 can be induced from the linear or angular motion of a trigger 114 using gears, linkages, bearings, and/or the like. FIG. 24 shows a bearing surface fixed to a trigger 114 pushing a helix-shaped bearing surface 72 on the surface of a torsional cylinder 69. FIGS. 23 and 24 show details of the bearing interaction between peg 70 on the translating trigger 114 and the rotating cylinder 69. A torsional spring 71 provides the constraint to return the cam 68 and shaft 67 to the un-actuated position against the motion of the trigger 114.

Figure 25:
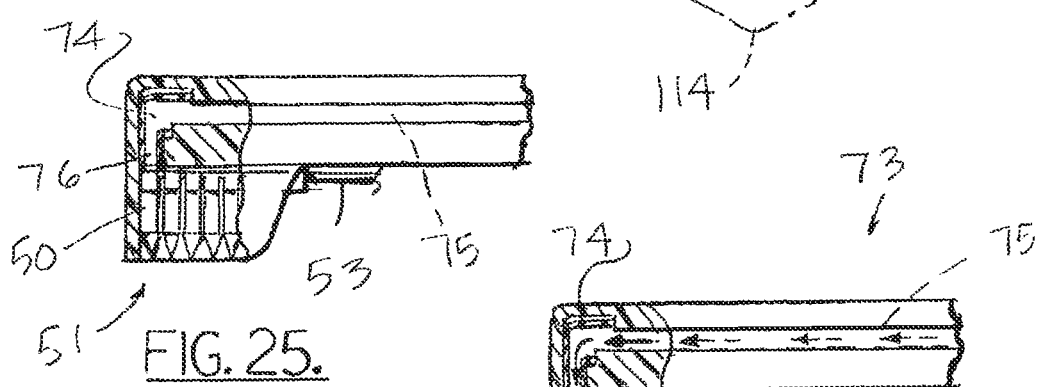
FIG. 25 is a partial, sectional, elevation view of a fourth embodiment of the apparatus of the present invention.
Figure 26:
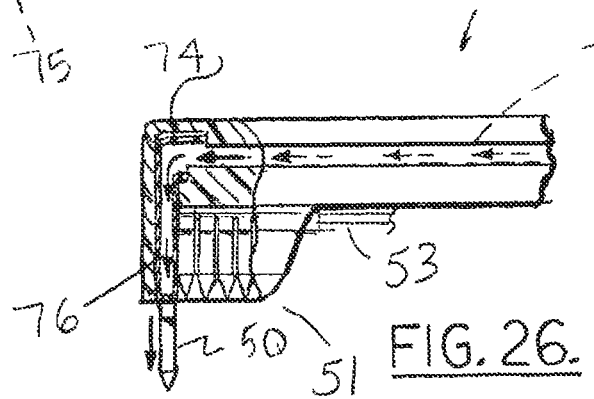
FIG. 26 is a partial, sectional, elevation view of a fourth embodiment of the apparatus of the present invention.

Another variant shown in FIGS. 25 and 26 and designated by the numeral 73 is configured to fire staples utilizing the resultant force from pressurizing a cavity. This can be accomplished with either a gas (e.g., air for a pneumatic device) or a liquid (e.g., water for a hydraulic device). The cavity 74 can be the space adjacent the staple 50, sealed with a translating surface (e.g., a piston), an expanding bladder (e.g., a balloon or diaphragm), or combination of the two. The liquid or gas system can either be closed or open. An open system would vent the pressurized medium when the staple exits, e.g., through an orifice normally sealed by a staple. A closed system, such as the embodiment depicted in FIGS. 25 and 26, would use the motion of a trigger to push water down a pressurization tube 75 and expand an elastic balloon 76 into a volume which displaces the staple to be fired from the staple bank 51. FIG. 25 shows the balloon 76 in the ready, contracted state. FIG. 26 shows the balloon 76 in the inflated, stapling state.

It should be understood that the staple 50 can be any shape that will be passed through the mucosal bilayer of the nasal septum and may include cartilage between the mucosal layer. This staple 50 will pull the mucosal layers in proximity preventing the formation of a hematoma. The staple 50 will preferably be made of an absorbable material such as polyglycolic acid (PGA) or polylactic acid (PLA) or may be made as a combination of copolymers.

The stapler and staples may be produced and packaged in a sterile environment or sterilized before use. A range of options is available and the choice will depend in part on the particular component materials employed. Irradiation, as with gamma rays or electron beams, can be used assuming all components are compatible, particularly component rubbers and plastics. Exposure to sterilizing gasses, such as ethylene oxide, maybe used, as long as component plastics do not retain amounts which exceed accepted levels. Likewise, liquids may also be used, such as those containing glutaraldehyde, in accordance with accepted standards.

The present invention can also include a nasal spray which facilitates the absorption of the staple polymer. The spray is preferably made of ingredients that will maintain moisture in the nasal cavity such as saline, but will also be formulated to increase degradation of the staple 50 which may include either a base or acid, an enzyme such as pepsin, or the formulation may be hypertonic to pull moisture into the nasal cavity. The nasal spray is preferably used around 6-8 times per day for 4-6 weeks (or until the staples 50 are completely absorbed).

PARTS LIST

The following is a list of parts and materials suitable for use in the present invention:

| Part Number | Description |
|---|---|
| 10 | septal stapler apparatus |
| 11 | tool body (unfilled or filled plastic such as ABS, PVC, polypropylene, polyester or polycarbonate, or metal such as aluminum, stainless steel, or titanium - e.g. 7-15 cm long, 2-6 cm high, and 2-5 cm wide) |
| 12 | proximal end portion |
| 13 | distal end portion |
| 14 | trigger (unfilled or filled plastic such as ABS, PVC, polypropylene, polyester or polycarbonate, or metal such as aluminum, stainless steel, or titanium - e.g. 1-5 cm long, 1-4 cm high, and 1-4 cm wide) |
| 15 | moving or tensioning arm (unfilled or filled plastic such as ABS, PVC, polypropylene, polyester or polycarbonate, or metal such as aluminum, stainless steel, or titanium - e.g. 5-16 cm long, 2-8 mm high, and 1-5 mm wide) |
| 16 | fixed arm (unfilled or filled plastic such as ABS, PVC, polypropylene, polyester or polycarbonate, or metal such as aluminum, stainless steel, or titanium - e.g. 5-16 cm long, 2-8 mm high, and 1-5 mm wide) |
| 17 | proximal end portion |
| 18 | distal end portion |
| 19 | receptacle |
| 20 | socket |
| 21 | contoured section |
| 22 | concavity |
| 23 | projection |
| 24 | camming surface |
| 25 | trigger spring (such as model no. CO240-020-2000-S produced by Associated Spring Raymond, a subsidiary of Barnes Group, Inc. of 1705 Indian Wood Circle, Maumee, OH 43537, US) |
| 26 | cylinder |
| 27 | cylinder |
| 28 | lever (unfilled or filled plastic such as ABS, PVC, polypropylene, polyester or polycarbonate, or metal such as aluminum, stainless steel, or titanium - e.g. 1-2 cm long, 1-4 mm high, and 1-4 mm wide) |
| 29 | lower end portion |
| 30 | fulcrum |
| 31 | central portion |
| 32 | transverse pin |
| 33 | upper end portion |
| 34 | staple actuator link (unfilled or filled plastic such as ABS, PVC, polypropylene, polyester or polycarbonate, or metal such as aluminum, stainless steel, or titanium - e.g. 5-16 cm long, 2-8 mm high, and 1-5 mm wide) |
| 35 | proximal end |
| 36 | distal end |
| 37 | spring (such as model no. E0063-007-0250-S produced by Associated Spring Raymond, a subsidiary of Barnes Group, Inc. of 1705 Indian Wood Circle, Maumee, OH 43537, US) |
| 38 | hook |
| 39 | hook |
| 40 | slotted portion |
| 41 | rectangular head (unfilled or filled plastic such as ABS, PVC, polypropylene, polyester or polycarbonate, or metal such as aluminum, stainless steel, or titanium - e.g. 3-8 mm long, 3-8 mm wide, and 0.5-1.5 mm thick) |
| 42 | pivotal connection |
| 43 | transverse bar |
| 44 | longitudinal slot |
| 46 | transverse slot |
| 47 | curved slot section |
| 48 | user |
| 49 | arrow |
| 50 | staple (bio-absorbable polymers or copolymers such as polyglycolic acid (PGA), polylactic acid (PLA), polydioxanone, polycaprolactone, polyhydroxybutyrate, polyester, or other polymer such as PVC, polypropylene, or polycarbonate, or metal such as aluminum, stainless steel, or titanium - e.g. 2-6 mm long and 0.5-2.5 mm thick) |
| 51 | staple bank |
| 52 | pointed section |
| 53 | staple advance rod (unfilled or filled plastic such as ABS, PVC, polypropylene, polyester or polycarbonate, or metal such as aluminum, stainless steel, or titanium - e.g. 4-10 cm long, 0.5-5 mm high, and 0.5-5 mm wide) |
| 54 | advance rod spring (such as model no. C0057-006-0310-S produced by Associated Spring Raymond, a subsidiary of Barnes Group, Inc. of 1705 Indian Wood Circle, Maumee, OH 43537, US) |
| 55 | enlarged head |
| 56 | arrow |
| 57 | rod |
| 58 | transverse beam |
| 59 | mucosal membrane layer |
| 60 | mucosal membrane layer |
| 61 | septal stapler apparatus |
| 62 | magnet |
| 64 | leaf spring (unfilled or filled plastic such as ABS, PVC, polypropylene, polyester or polycarbonate, or metal such as aluminum, stainless steel, or titanium - e.g. 1-10 mm long, 0.1-2 mm high, and 0.1-2 mm wide) |
| 65 | plunger (a magnetic material containing such substances as iron, nickel, cobalt, wairauite, magnetite, oxides, or sulfides in whole or in part) |
| 66 | variant with cam |
| 67 | shaft (unfilled or filled plastic such as ABS, PVC, polypropylene, polyester or polycarbonate, or metal such as aluminum, stainless steel, or titanium - e.g. 5-16 cm long, 2-4 mm diameter,) |
| 68 | cam (unfilled or filled plastic such as ABS, PVC, polypropylene, polyester or polycarbonate, or metal such as aluminum, stainless steel, or titanium - e.g. 3-8 mm long, 0.5-2 mm thick, and 0.5-2 mm wide) |
| 69 | cylinder (unfilled or filled plastic such as ABS, PVC, polypropylene, polyester or polycarbonate, or metal such as aluminum, stainless steel, or titanium - e.g. 1-3 cm long, 1-2 cm diameter) |
| 70 | peg |
| 71 | torsional spring |
| 72 | bearing surface |
| 73 | variant with pressure |
| 74 | cavity |
| 75 | pressurization tube |
| 76 | balloon (an elastic material such as rubber, latex or silicone) |
| 77 | cavity |
| 114 | trigger (unfilled or filled plastic such as ABS, PVC, polypropylene, polyester or polycarbonate, or metal such as aluminum, stainless steel, or titanium - e.g. 1-5 cm long, 1-4 cm high, and 1-4 cm wide) |

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

What is claimed is:

1. A method comprising:
    obtaining a nasal septal stapling apparatus comprising:
        a body;
        a first arm extending from the body and comprising an end distal from the body, the first arm being fixed relative to the body;
        a second arm extending from the body, the second arm being movable relative to the body and being spaced apart from the first arm to receive a nasal septum of a patient;
        a staple head coupled to the end of the first arm, wherein the staple head is adapted to receive a staple bank comprises a plurality of staples;
        a staple moving member configured to discharge a staple from the staple bank; and
        a trigger movably mounted to the body and configured to move from a resting position to an intermediate position and configured to move from the intermediate position to a firing position wherein
            the second arm is moved toward the first arm when the trigger is moved from the resting position to the intermediate position;
            the staple moving member does not discharge a staple when the trigger is moved from the resting position to the intermediate position; and
            the staple moving member discharges a staple when the trigger is moved from the intermediate position to the firing position;
    inserting a staple bank comprising a plurality of staples into the staple head;
    placing one of the first and second arms against a first side of the nasal septum of a patient and the other of the first or second arms against an opposite side of the nasal septum; and
    moving the trigger to the firing position to cause the staple moving member to discharge a staple from the staple bank and through the nasal septum of the patient.

2. The method of claim 1, wherein the trigger is configured to engage a lever when the trigger is in the intermediate position.

3. The method of claim 2, wherein the lever is configured to rotate when the trigger is moved from the intermediate position to the firing position.

4. The method of claim 3 wherein:
    an actuator link includes the staple moving member; and
    the lever is configured to engage the actuator link and move the actuator link when the trigger is moved from the intermediate position to the firing position.

5. The method of claim 3, wherein the lever is configured to rotate about a fulcrum when the trigger is moved from the intermediate position to the firing position.

6. The method of claim 1, wherein:
    the second arm comprises a contoured section; and
    the trigger comprises a camming surface configured to engage the contoured section of the moving arm when the trigger is in the resting position.

7. The method of claim 6, wherein the camming surface of the trigger is disengaged from the contoured section of the moving arm when the trigger is in the intermediate position.

8. The method of claim 1, wherein the first arm is configured for insertion into a first nasal passageway and wherein the second arm is configured for insertion into a second nasal passageway.

9. The method of claim 1, wherein a distal end of the second arm is in contact with the first end of the first arm when the trigger is in the intermediate position and when the trigger is in the firing position.

10. The method of claim 1, wherein the second arm comprises a distal end portion having a receptacle configured to receive a staple that is discharged from the staple bank.

11. A method comprising:
    obtaining a nasal septal stapling apparatus comprising:
        a body;
        a trigger movably mounted to the body and being configured to move in a first direction from a resting position to a firing position;
        a fixed arm extending from the body, the fixed arm comprising a first end staple head for receiving a staple bank comprising a plurality of staples distal from the body;
        a moving arm extending from the body, the moving arm being spaced apart from the fixed arm to receive a nasal septum of a patient and being configured to move toward the fixed arm when the trigger is moved from the resting position to the firing position; and
        an actuator link configured to move in a second direction when the trigger is moved from the resting position to the firing position, wherein:
            the second direction of movement for the actuator link is toward the first end of the fixed arm; and
            the first direction of movement for the trigger is away from the first end of the fixed arm;
    inserting a staple bank comprising a plurality of staples into the staple head;
    placing one of the fixed or moving arms against a first side of the nasal septum of a patient and the other of the fixed or moving arms against an opposite side of the nasal septum; and
    moving the trigger, wherein moving the trigger causes the actuator link to discharge a staple from the staple bank and through the nasal septum of the patient.

12. The method of claim 11, wherein the actuator link is configured to engage a staple and push the staple away from the first end of the fixed arm when the trigger is moved from the resting position to the firing position.

13. The method of claim 11, wherein the fixed arm comprises a slot configured to receive the actuator link.

14. The method of claim 13, wherein the slot comprises a first portion that is parallel to a portion of the fixed arm extending between the body and the first end of the fixed arm.

15. The method of claim 14, wherein the slot comprises a second portion that is perpendicular to a portion of the fixed arm extending between the body and the first end of the fixed arm.

16. The method of claim 15, wherein the slot comprises a curved portion between the first portion and the second portion.

17. The method of claim 11, wherein:
    the moving arm comprises a contoured section; and
    the trigger comprises a camming surface configured to engage the contoured section of the moving arm when the trigger is in the resting position.

18. The method of claim 17, wherein the camming surface of the trigger is disengaged from the contoured section of the moving arm when the trigger is in the firing position.

19. The method of claim 1, wherein the patient is a human.

* * * * *

UNITED STATES PATENT AND TRADEMARK OFFICE
CERTIFICATE OF CORRECTION

| | | |
|---|---|---|
| PATENT NO. | : 9,241,726 B2 | Page 1 of 1 |
| APPLICATION NO. | : 14/059882 | |
| DATED | : January 26, 2016 | |
| INVENTOR(S) | : Michael C. Larson | |

It is certified that error appears in the above-identified patent and that said Letters Patent is hereby corrected as shown below:

Claims

Claim 11, column 10, line 15:

Delete "first end".

Signed and Sealed this
Seventh Day of June, 2016

Michelle K. Lee
*Director of the United States Patent and Trademark Office*